US012807323B2

(12) United States Patent
Coulson et al.

(10) Patent No.: US 12,807,323 B2
(45) **Date of Patent: *Nov. 24, 2026**

(54) AIRPLANE FUEL CONTAMINANT DETECTION SYSTEM

(71) Applicant: Coulson Aviation (USA) Inc, Portland, OR (US)

(72) Inventors: Britton Coulson, Port Alberni (CA); Wayne Coulson, Port Alberni (CA)

( * ) Notice: Subject to any disclaimer, the term of this patent is extended or adjusted under 35 U.S.C. 154(b) by 0 days.

This patent is subject to a terminal disclaimer.

(21) Appl. No.: 19/397,436

(22) Filed: Nov. 21, 2025

(65) Prior Publication Data

US 2026/0077877 A1 Mar. 19, 2026

Related U.S. Application Data

(63) Continuation of application No. 18/819,741, filed on Aug. 29, 2024, now Pat. No. 12,479,589.

(51) Int. Cl.

| | |
|---|---|
| ***B64D 37/18*** | (2006.01) |
| ***B64F 5/60*** | (2017.01) |
| ***G01N 33/22*** | (2006.01) |

(52) U.S. Cl.

CPC ................ *B64D 37/18* (2013.01); *B64F 5/60* (2017.01); *G01N 33/22* (2013.01)

(58) Field of Classification Search

CPC ............ B64D 37/18; B64F 5/60; G01N 33/22

See application file for complete search history.

(56) References Cited

U.S. PATENT DOCUMENTS

| | | | | |
|---|---|---|---|---|
| 6,871,677 | B2 * | 3/2005 | Zerangue, Sr. ........ | B60K 15/04 141/96 |
| 7,518,719 | B2 | 4/2009 | Sprenger et al. | |
| 8,381,779 | B1 | 2/2013 | Wyler | |
| 8,498,750 | B2 | 7/2013 | Stevens et al. | |
| 8,684,028 | B2 | 4/2014 | Perez | |
| 8,720,499 | B2 | 5/2014 | Kastner et al. | |
| 9,109,940 | B2 | 8/2015 | Bahorich et al. | |
| 12,479,589 | B1 * | 11/2025 | Coulson ................ | B64D 37/18 |

(Continued)

FOREIGN PATENT DOCUMENTS

| | | | |
|---|---|---|---|
| CN | 202928658 | U | 5/2013 |
| CN | 107131924 | A | 9/2017 |

(Continued)

OTHER PUBLICATIONS

ASTM International, Standard Specification for Aviation Turbine Fuels, 2005, 6 pages.

(Continued)

*Primary Examiner* — Donald J Wallace

(74) *Attorney, Agent, or Firm* — Sterne, Kessler, Goldstein & Fox P.L.L.C.

(57) ABSTRACT

An aircraft-based fuel quality monitoring and alerting system is disclosed herein. The aircraft-based fuel quality monitoring and alerting system can include a first sensor configured to output a signal associated with contamination of fuel entering an aircraft through a first fuel inlet. The system can further include a processor configured to determine a first contamination level of the fuel based on the signal and an alerting system configured to deliver an alert if the first contamination level is outside a predetermined range.

25 Claims, 7 Drawing Sheets

(56) References Cited

U.S. PATENT DOCUMENTS

| | | | |
|---|---|---|---|
| 2002/0040593 A1 | 4/2002 | Schaefer et al. | |
| 2011/0115649 A1 | 5/2011 | Smith et al. | |
| 2011/0130882 A1 | 6/2011 | Perez | |
| 2011/0162448 A1 | 7/2011 | McGaughey et al. | |
| 2012/0234770 A1 | 9/2012 | Goodwin | |
| 2013/0079955 A1 | 3/2013 | Masiello et al. | |
| 2014/0039777 A1 | 2/2014 | Geng et al. | |
| 2015/0123820 A1 | 5/2015 | Merle et al. | |
| 2015/0301013 A1 | 10/2015 | Wiebe | |
| 2018/0005533 A1* | 1/2018 | Lohmiller | G05D 1/0011 |
| 2019/0127080 A1 | 5/2019 | Selvarajan et al. | |
| 2022/0107303 A1 | 4/2022 | Goltzman et al. | |
| 2024/0190579 A1 | 6/2024 | Fallon | |
| 2024/0321113 A1 | 9/2024 | Feyereisen et al. | |
| 2025/0110060 A1 | 4/2025 | Venkata et al. | |

FOREIGN PATENT DOCUMENTS

| | | |
|---|---|---|
| CN | 113945255 A | 1/2022 |
| CN | 116238324 A | 6/2023 |
| GB | 2625124 A | 6/2024 |

OTHER PUBLICATIONS

Avfuel, Rampside Training System, Video reference guide, May 7, 2014, 91 pages.

Parker Velcon, Water-in-Fuel Sensor (WIF), 2019, 2 pages.

Parker Velcon, VCA Fuel Condition Monitoring & Control, 2015, 24 pages.

International Search Report and Written Opinion issued under International Application No. PCT/US2025/043546, mailed Oct. 8, 2025, 10 Pages.

* cited by examiner

AIRPLANE FUEL CONTAMINANT DETECTION SYSTEM

CROSS REFERENCE TO RELATED APPLICATIONS

This application is a continuation of and claims priority to US Application No. Ser. No. 18/819,741, filed Aug. 29, 2024, which is incorporated herein in its entirety by reference.

FIELD

The present disclosure is directed to fuel quality monitoring and alerting systems. More specifically, the present disclosure is directed to fuel quality monitoring and alerting systems including components installed on aircraft, such as airplanes and helicopters.

BACKGROUND

Poor fuel quality can be associated with the presence of contaminants, such as water and particulates, in a fuel tank. Poor fuel quality can also be characterized by an inappropriate fuel type that is, for example, a different or lower grade than desirable for the engine. Poor fuel quality can cause failures of components or the entire engine in a variety of vehicles and circumstances, including airborne aircraft.

BRIEF SUMMARY OF THE DISCLOSURE

Poor fuel quality can originate from a fuel source, such as a fuel truck. If the fuel source is contaminated, a vehicle receiving fuel from the fuel source may intake contaminated fuel that can cause premature failures. For example, if an aircraft receives fuel contaminated with water, the water may freeze as the aircraft gains altitude. Water is denser than, for example, jet fuel, and can therefore settle between the jet fuel and the engine. If the water freezes, it can prevent the flow of fuel into the engine, which can cause an engine failure. As another example, a fuel source may contain a different or lower grade of fuel than is desirable, or prescribed by the engine manufacturer, for proper functioning of the engine, and can cause premature wear and subcomponent damage. Also, a jet engine can be inadvertently exposed to aviation gas (Avgas) instead of turbine fuel, and a piston-engine aircraft can be inadvertently exposed to turbine fuel. Manual sampling techniques to observe or measure fuel quality may not provide a timely indication of contamination. For example, it can take about an hour for water to settle to the bottom of an aircraft fuel tank filled with turbine fuel. Sumping fuel from a low point on the aircraft before the water settles may provide a false indication of fuel quality. Thus, it is possible for an aircraft to takeoff before being able to manually detect contamination. Contaminated fuel, including particulates, water, and improper fuel types, can cause an engine to malfunction or fail.

The present disclosure is directed to aircraft-based fuel quality monitoring and alerting systems. In some embodiments, the system includes a sensor configured to output a signal associated with contamination of fuel entering an aircraft through an inlet. The system can further include a processor configured to determine a contamination level of the fuel entering the aircraft based on the output signal. The system can also include an alerting system configured to deliver an alert if the contamination level is outside a predetermined range.

In some embodiments, the system can include a second sensor configured to output a signal associated with contamination of the fuel when the fuel enters the aircraft. Additionally, the system can include a processor configured to determine a second contamination level of the fuel entering the aircraft. In some embodiments, the system can be configured to deliver an alert if the first contamination level is outside the predetermined range and the second contamination level is outside the predetermined range. In some embodiments, the first sensor and second sensor can be disposed inside a first fuel tank inside the aircraft. The first sensor can be disposed within a first wing, and the second sensor can be disposed within a second wing. In some embodiments, the first sensor can be configured to output signals associated with a contamination level of fuel entering a first fuel inlet formed in a first wing, and the second sensor can be configured to output signals associated with a contamination level of fuel entering a second fuel inlet formed in a second wing. In some embodiments, the first and second sensor can be disposed inside an aircraft fuel tank. In some embodiments, the first sensor can be disposed in a first aircraft fuel tank in a first wing, and the second sensor can be disposed in a second aircraft fuel tank in a second wing.

In some embodiments, the alerting system of the present disclosure is configured to deliver a visual alert. In some embodiments, the visual alert can be a text alert. In some embodiments, the alerting system can deliver an aural alert. In some embodiments, the alerting system can be configured to deliver a combination of a visual alert and an aural alert.

In some embodiments, the alerting system can be configured to deliver an alert when a contamination level is outside a predetermined range, and the contamination level can be associated with an amount of water entering the aircraft through the a fuel inlet. In some embodiments, the predetermined range can include an amount of water entering the aircraft though a fuel inlet. In some embodiments, the predetermined range can be between 0 PPM and 15 PPM of water. In some embodiments, the processor can be configured to determine the amount of water in the fuel entering the aircraft fuel tank.

In some embodiments, the alerting system of the present disclosure can be configured to deliver an alert to a pilot interface, including a display, indicator, and/or audio system. In some embodiments, the alerting system can be configured to deliver the alert through a wireless communication protocol, such as Bluetooth, WiFi, and/or RF. In some embodiments, the alerting system can deliver an alert from the aircraft to a ground station, such as a ground control station configured to operate a remotely piloted aircraft.

In some embodiments, an aircraft includes a first sensor configured to output a signal associated with contamination of fuel entering an aircraft through a first fuel inlet, a processor configured to determine a first contamination level of the fuel based on the signal, and an alerting system configured to deliver an alert if the first contamination level is outside a predetermined range. In some embodiments, the aircraft can have a fuel inlet formed in a wing, and the first sensor can be disposed in fuel tank in the wing.

The present disclosure is also directed a method for monitoring aircraft fuel quality. In some embodiments, the method can include outputting, by a sensor disposed in an aircraft, a signal associated with contamination of fuel entering an aircraft through a fuel inlet; determining, by a processor, a contamination level of the fuel based on the signal; and delivering an alert, by an alerting system, if the contamination level is outside a predetermined range.

In some embodiments, the alerting system of the present disclosure can be configured to deliver an alert if the contamination level is outside the predetermined range for a predetermined time period. In some embodiments, the alerting system can deliver a first alert if the contamination level is outside the predetermined range for a first predetermined time period, and the alerting system can deliver a second alert if the contamination level is outside the predetermined range for a second predetermined time period. In some embodiments, the first alert is different from the second alert. For example, the first alert can be a visual alert, and the second alert can be an aural alert. In some embodiments, the alerting system can be configured to deliver a first alert if the contamination level is outside a first predetermined range, and to deliver a second alert if the contamination level is outside a second predetermined range, wherein the first predetermined range is different than the second predetermined range. For example, the first predetermined range can be associated with a smaller portion of water entering the fuel tank than the second predetermined range.

DETAILED DESCRIPTION

The present disclosure describes monitoring fuel quality during fueling and delivering an alert, for example, to a crew, such as a flight crew onboard the aircraft. In some embodiments, the fuel quality monitoring and alerting systems disclosed herein delivers an alert to a crew on a ground control station, such as a ground control station configured to operate a remotely piloted aircraft. The embodiments disclosed herein provide timely, accurate, alerts during fueling to prevent the continued input of contaminated fuel.

Figure 1:
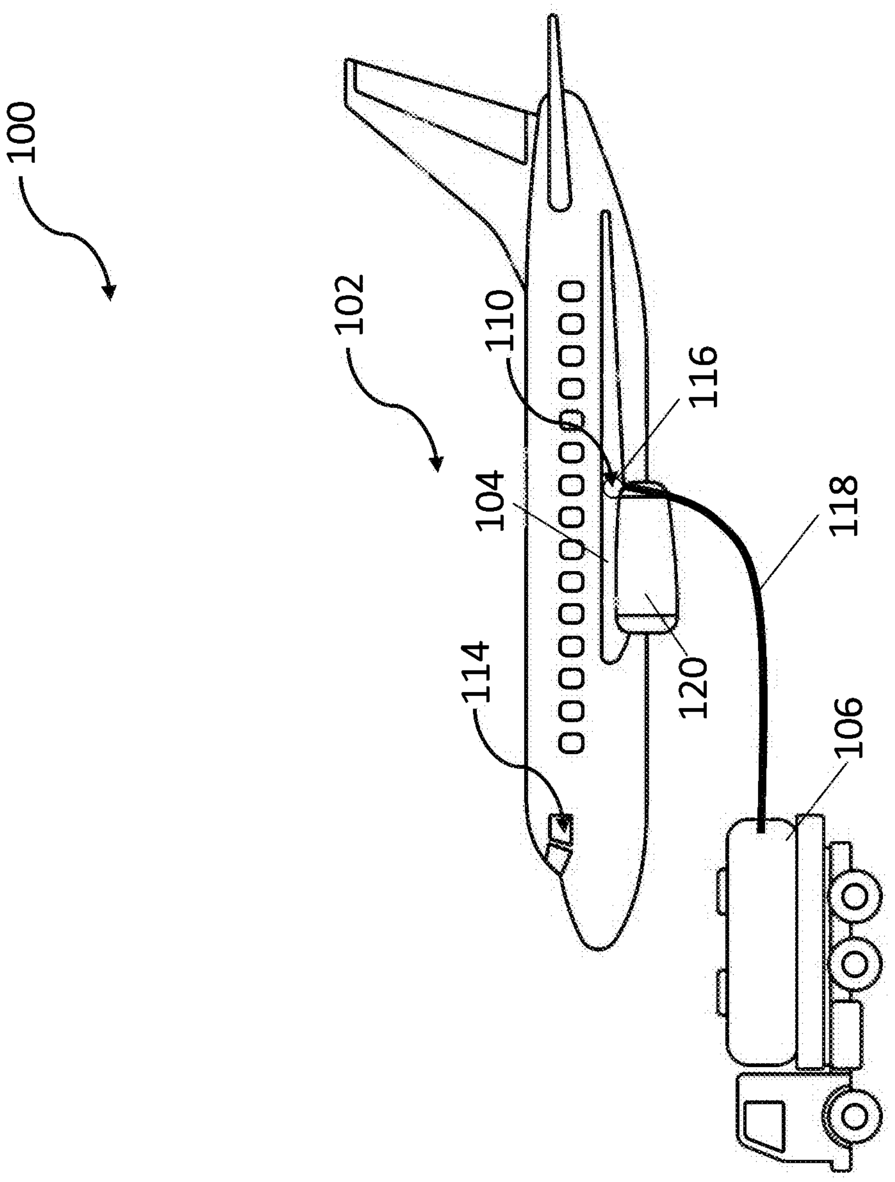
FIG. 1 illustrates a fuel quality monitoring and alerting system for an aircraft according to an embodiment.

FIG. 1 illustrates a fuel quality monitoring system 100 configured to monitor fuel quality as fuel enters an aircraft 102 from a fuel source 106. In some embodiments, fuel quality monitoring system 100 can be an aircraft-based system having one or more components installed on aircraft 100. As a result, fuel quality monitoring system 100 can alert, for example, a flight crew onboard aircraft 102, that fuel entering aircraft 102 is contaminated. For example, fuel can enter an aircraft fuel tank 104 through a fuel inlet 116. The fuel can enter fuel inlet 116 from fuel source 106 through a fuel line 118. Fuel source 106 can be, for example, a fuel truck or a fixed fueling station. In some embodiments, the fuel source can be another aircraft, such as an aircraft configured for aerial refueling.

Fuel stored in fuel source 106 can be contaminated when, for example, fuel source 106 contains water, an improper fuel type, or other particulates. Contaminants can enter an aircraft fuel tank 104 through fuel line 118, which can cause an engine 120 to malfunction if, for example, water freezes during flight and blocks fuel from entering engine 120.

To deliver an alert of contaminated fuel entering aircraft 102, fuel quality monitoring system 100 can include a sensor 110 configured to output signals associated with the contamination of fuel entering aircraft 102. In some embodiments, sensor 110 can be disposed in fuel inlet 116. In some embodiments, sensor 110 can be disposed in aircraft fuel tank 104. Sensor 110 can be any sensor configured to output signals associated with contamination levels of a fuel. In some embodiments, sensor 110 is part of an optical system configured to output signals associated with the light entering the sensor at a predetermined angle. In some embodiments, sensor 110 can be a pressure sensor. In some embodiments, sensor 110 can form part of an electrical system configured to output signals associated with the resistance of a fluid.

Depending on the contamination of the fuel entering aircraft fuel tank 104, fuel quality monitoring system 100 can deliver an alert, for example, via a pilot interface 114. Pilot interface 114 can be, for example, a display configured to output text, an indicator such as a light, and/or a speaker system configured to output an aural alert. Although FIG. 1 illustrates pilot interface 114 inside aircraft 102, pilot interface 114 can be separate from aircraft 102. For example, in some embodiments, aircraft 102 is a remotely piloted aircraft and pilot interface 114 is part of a ground control station configured to operate a remotely piloted aircraft. For example, pilot interface 114 can be part of a ground control station located near a first airport, and aircraft 102 can be located and receiving fuel at a second airport. In some embodiments, pilot interface includes an electronic flight bag, such as a mobile device or tablet, configured to execute a software application. Although FIG. 1 illustrates a fixed-wing aircraft, aircraft 102 can be a helicopter, tiltrotor, or any other aircraft configured to receive fuel.

Figure 2:
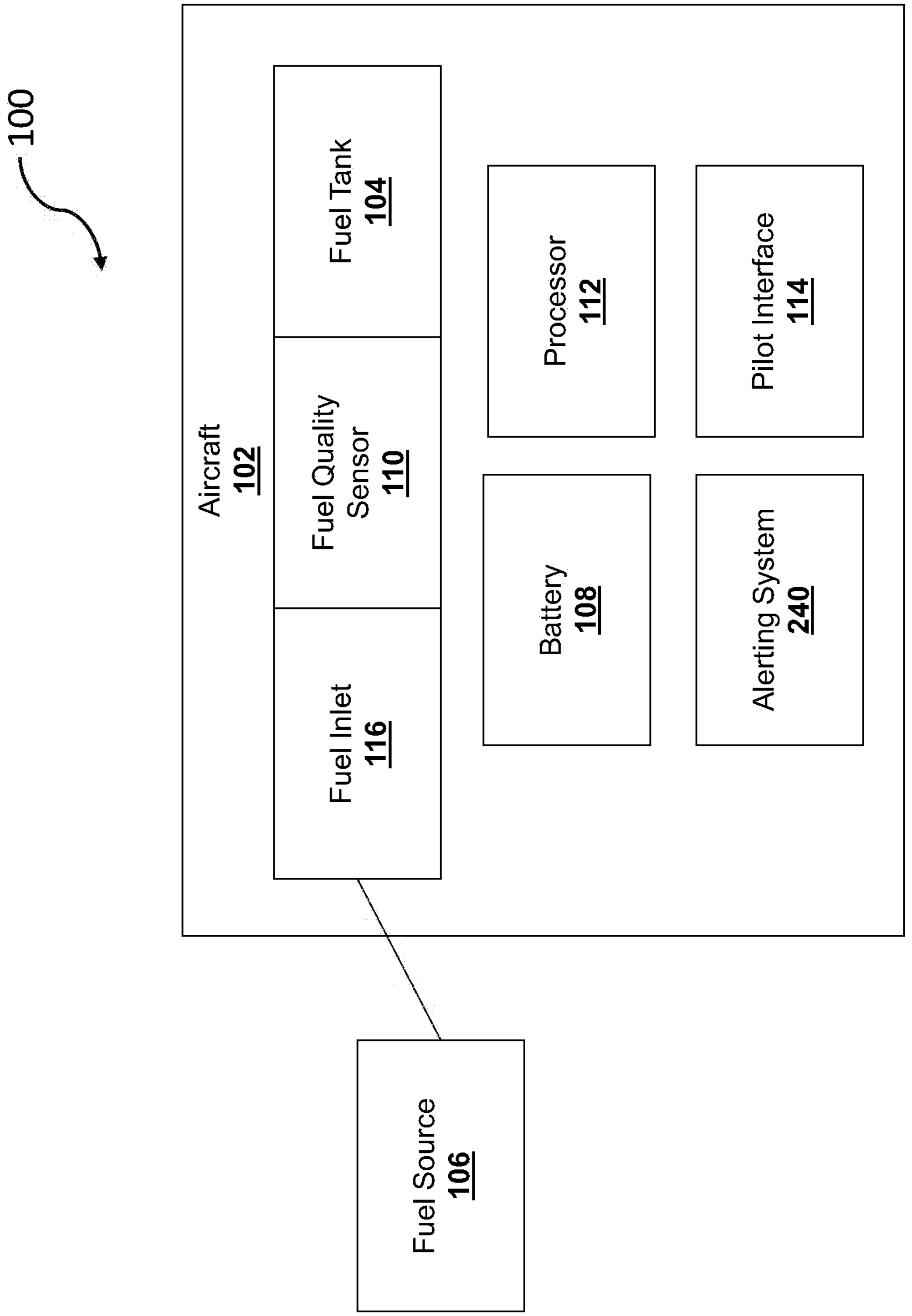
FIG. 2 illustrates a system block diagram of the fuel quality monitoring and alerting system according to an embodiment.
Figure 3:
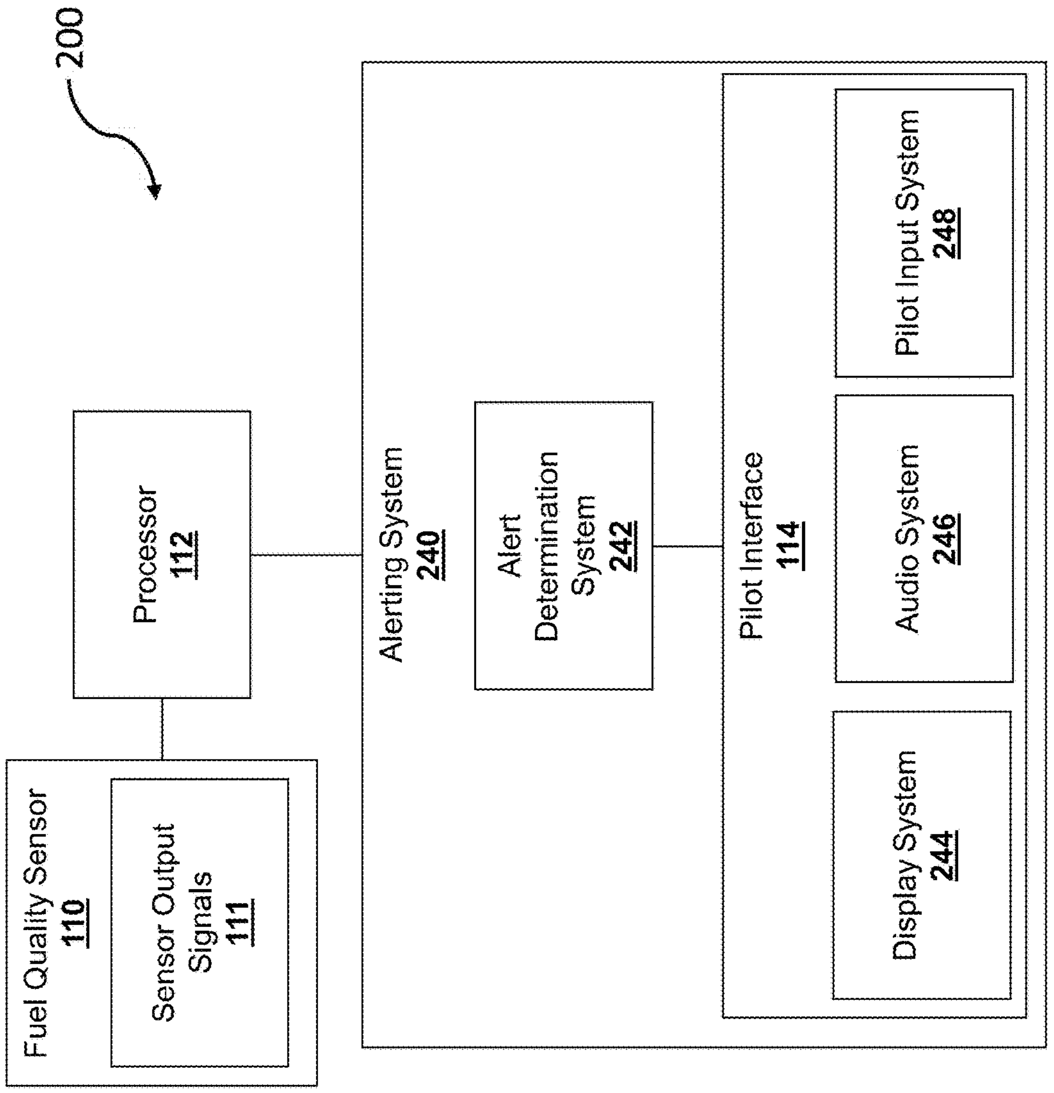
FIG. 3 illustrates a system block diagram of sub-systems of the fuel quality monitoring and alerting system according to an embodiment.

As shown in FIGS. 2-3, for example, fuel quality monitoring system 100 can include a battery 108, a processor 112, and an alerting system 240. Battery 108 can be, for example, auxiliary power unit configured to power electrical systems in aircraft 102. In some embodiments, battery 108 can be configured to power processor 112 and a separate battery can be configured to power other electrical systems, such as the flight display, speakers, autopilot, and passenger entertainment devices. In some embodiments, battery 108 can power processor 112 and alerting system 240. In some embodiments, a first battery can power processor 112 and a second battery can power alerting system 240.

In some embodiments, as shown in FIG. 3, fuel quality sensor 110, processor 112, and alerting system 240 can be characterized as a sub-system 200. Processor 112 can be configured to determine contamination levels of fuel entering aircraft fuel tank 104 based on sensor output signals 111 output by one or more sensors 110. Alerting system 240 can be configured to receive contamination levels from processor 112. In some embodiments, processor 112 executes alerting system 240. In some embodiments, a first processor determines a contamination level of the fuel entering aircraft 102, and a second processor executes alerting system 240.

Alerting system 240 can include an alert determination system 242. Alert determination system 242 can determine if an alerting condition is satisfied based on the contamination levels determined by processor 112. In some embodiments, alert determination system 242 can be configured to determine that an alerting condition is satisfied if the contamination level is outside a predetermined range, for example, above or below a threshold value. Further, alerting system 240 can be configured to deliver an alert if the contamination level is outside a predetermined range. In some embodiments, the predetermined range can be, for example, between 0 and 20 PPM of water. In some embodiments, the predetermined range can be, for example, between 0 and 15 PPM of water. In some embodiments, the predetermined range can be, for example, between 0 and 10 PPM of water.

Alerting system 240 can deliver an alert to pilot interface 114. Pilot interface 114 can include a display system 244, an audio system 246, and/or a pilot input system 248. Display system 244 can be configured to output text, such as an alert reading "FUEL," "POOR FUEL QUALITY," "STOP FUEL," "CHECK FUEL," "CONTAMINATED FUEL," or any other message that can inform a flight or operational crew that the fuel entering aircraft 102 is contaminated or of insufficient quality or grade. In some embodiments, display system 244 can be configured to output text in different colors indicating the severity of the contamination. For example, display system can be configured to output a first visual alert having a first color, and a second visual alert having a second color. Flight crews can understand the first color to indicate an advisory alert, and the second color to indicate a warning alert of higher urgency than the advisory alert. Display system 244 can include a Primary Flight Display, a Secondary Flight Display, a Multi-Function Display, an ADS-B Display a Multi-Function Control and Display Unit, a Heads-Up Display, or any other display in aircraft 102 or a ground control station.

Audio system 246 can be configured to output similar messages as display system 244 through a speaker, headset, and/or other audio output device. In some embodiments, audio system 246 can be configured to beep in addition to, or instead of, outputting a message. Audio system 246 can be a standalone alert output source, or can complement display system 244. For example, if a flight crew does not see a visual alert on display system 244 (e.g., within a set period of time), delivering an aural alert through audio system 246 can help increase the likelihood that the flight crew will act on the alert and stop fueling.

Pilot input system 248 can be configured to receive input from a crew to, for example, extinguish an alert, record data associated with an alert, and/or reset alerting system 240.

In some embodiments, pilot interface 114 includes an electronic flight bag including display system 244, audio system 246, pilot input system 248, or any combination therein. For example, alerting system 240 can be configured to deliver an alert to an electronic flight bag through a wireless communication protocol, such as Bluetooth or Wi-Fi. As another example, alerting system 240 can be stored on an electronic flight bag and accessible as a software application, and processor 112 can be configured to deliver contamination levels to the electronic flight bag. Not all aircraft are equipped with a pilot interface capable of receiving contamination levels from processor 112, and retrofitting such aircraft can be costly. Integrating subsystem 200 with pilot interface 114 including an electronic flight bag can allow aircraft owners and operators to equip a wide variety of aircraft with the fuel quality monitoring and alerting systems and methods disclosed herein.

Figure 4:
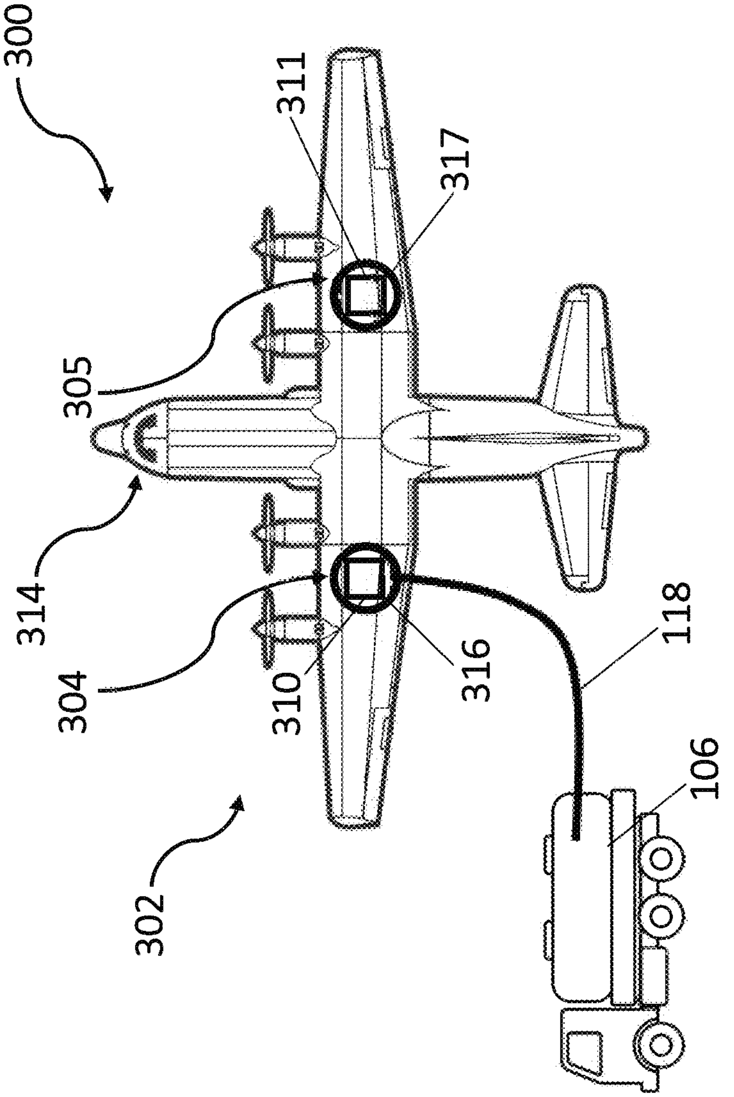
FIG. 4 illustrates a fuel quality monitoring and alerting system for an aircraft according to an embodiment.

In some embodiments, systems disclosed herein can be integrated on aircraft utilizing single point fueling, as illustrated in FIG. 1. Single point fueling typically involves delivering fuel through a single fuel inlet, for example, formed in a lower surface of a wing or the fuselage, and a valving system to direct it into the aircraft's fuel tank(s). However, not all aircraft are equipped with, or readily retrofit to include, a single point fueling system. The systems and methods disclosed herein can also be applied to aircraft configured for over-wing fueling, such as illustrated in FIG. 4. Over-wing fueling typically involves a fuel inlet formed on the top surface of each wing. Because each wing has a fuel inlet on its top surface, the fuel can flow into the aircraft's tanks under gravity.

As shown in FIG. 4, a fuel quality monitoring and alerting system 300 can include an aircraft 302 having a first fuel inlet 316 and a second fuel inlet 317. Both first fuel inlet 316 and second fuel inlet 317 can be formed in an upper surface of wings of aircraft 302. First fuel inlet 316 and second fuel inlet 317 can be configured to receive fuel, for example, from fuel source 106 via fuel line 118, which can engage first fuel inlet 316 and second fuel inlet 317 by extending over the wings on aircraft 302. For example, a fuel truck operator can place a ladder proximate to a first wing including first fuel inlet 316. Using the ladder, the fuel truck operator can raise the fuel line up to first fuel inlet 316 and dispense fuel into a first aircraft fuel tank 304. After dispensing fuel into first aircraft fuel tank 304, the fuel truck operator can reposition the ladder and raise fuel line 118 up to second fuel inlet 317 to dispense fuel into second aircraft fuel tank 305.

Aircraft 302 can include a first sensor 310 disposed in first fuel inlet 316 configured to output signals associated with contamination of fuel entering first aircraft fuel tank 304. Aircraft 302 can further include a second sensor 311 disposed in second fuel inlet 317 configured to output signals associated with contamination of fuel entering second aircraft fuel tank 305. Although the fuel entering first aircraft fuel tank 304 and second aircraft fuel tank 305 can come from the same fuel source 106, the contamination levels can be different. For example, if fuel source 106 contains water, the water can sink below the fuel because water is generally denser than fuels used to power jet and piston aircraft. If fuel line 118 draws fuel from a bottom of fuel source 106, first aircraft fuel tank 304 might intake water, and second aircraft fuel tank 305 might not because the water in fuel source 106 went into first aircraft fuel tank 304.

Accordingly, alerting system 240 can be configured to deliver an alert if the contamination level of the fuel entering first aircraft fuel tank 304 is outside a predetermined range and to deliver an alert if the contamination level of the fuel entering second aircraft fuel tank 305 is outside a predetermined range. Alerting system 240 can further be configured to output alerts associated with first aircraft fuel tank 304 and second aircraft fuel tank 305. For example, alerting system can be configured to output an aural alert announcing "RIGHT TANK FUEL," "CHECK RIGHT TANK FUEL," "STOP FUEL RIGHT TANK," CONTAMINATED FUEL RIGHT TANK," or any other message alerting the crew of contaminated fuel entering aircraft 302, and where the contaminated fuel is being dispensed.

Although the crew may be able to see which wing is receiving fuel when they receive an alert in some circumstances, some conditions can cause the flight crew's perception of the fueling to conflict with where alerting system 240 identified contaminated fuel. For example, as discussed in more detail below, alerting system 240 can be configured to deliver an alert if the contamination level is outside a predetermined range for a predetermined period. A fuel truck operator could switch to fueling a different tank during the predetermined period, and a location specific alert could direct the flight or ground crew to the first tank that received contaminated fuel. As another example, the flight or ground crew may be reviewing a pre-flight checklist and not actively looking at display system 244. By the time the crew sees the alert, the fuel truck operator could have switched to fueling a different tank, or could have completed fueling. Identifying the location of the contaminated fuel in aircraft having a multi-source fueling system can prevent flight crews from checking the wrong tank and concluding that the fuel quality is acceptable. Location specific alerts can also prevent crews from emptying both tanks, when only one tank contained contaminants, which can save time and reduce costs.

Figure 5:
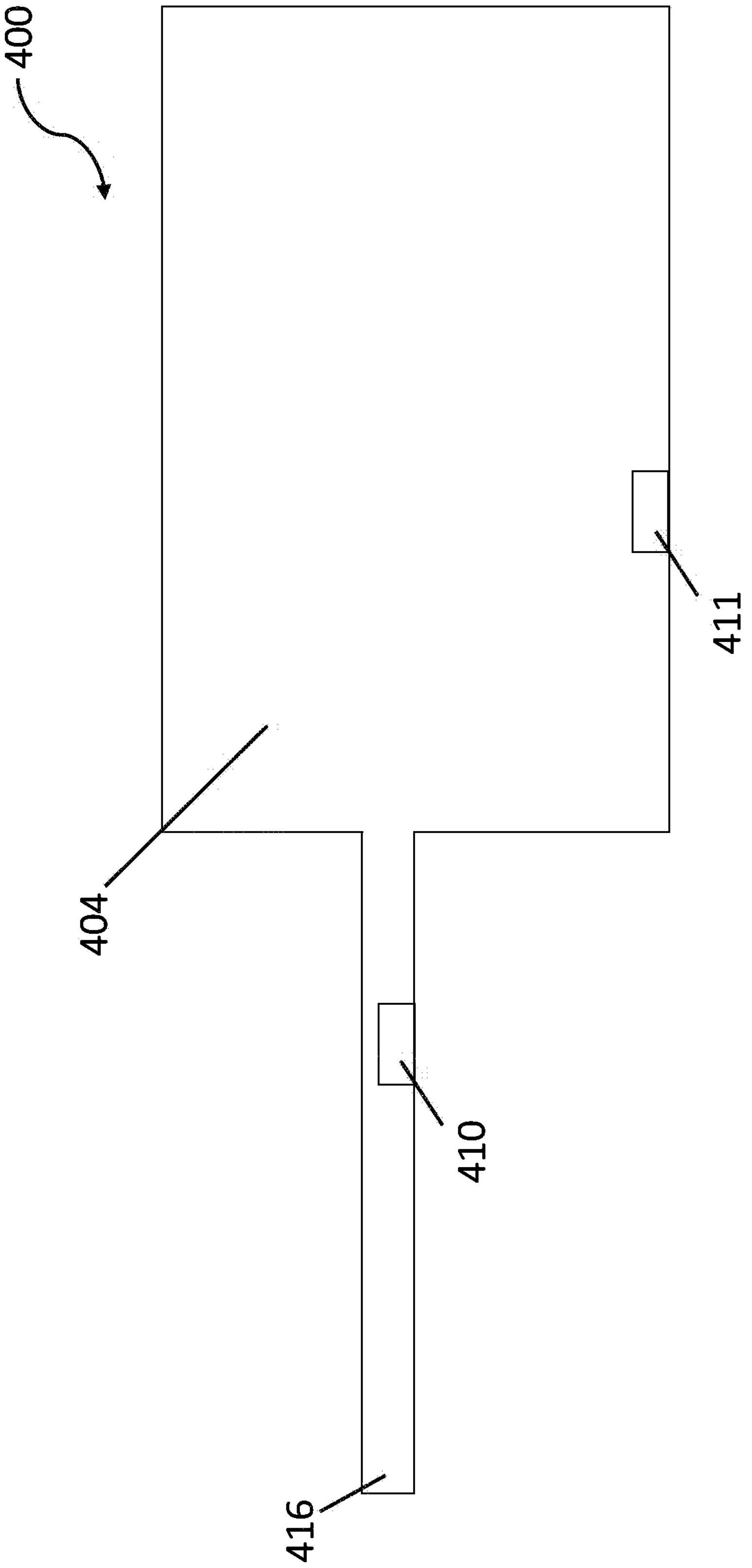
FIG. 5 illustrates a fuel tank with a fuel inlet according to an embodiment.

As shown for example in FIG. 5, in some embodiments, aircraft 102 can include a fuel system 400 having a first sensor 410 disposed in a fuel inlet 416 and/or a second sensor 411 disposed in aircraft fuel tank 404. First sensor 410 can be configured to output signals associated with the contamination of fuel entering fuel inlet 416, and second sensor 411 can be configured to output signals associated with the contamination level of fuel entering aircraft fuel tank 404. Although the fuel entering fuel inlet 416 is the same fuel entering aircraft fuel tank 404 shortly after passing fuel inlet 416, first sensor 410 and second sensor 411 can complement each other, or provide redundancy, to improve the accuracy of alerting system 240. For example, fuel passing through fuel inlet 416 can be more turbulent than the same fuel rising within aircraft fuel tank 404. Increased turbulence can result in unstable output signals from first sensor 410 caused by the rapid and volatile movement of fuel. Second sensor 411, while potentially exposed to a more stable fuel sample, can, however, introduce delays due to the time required for fuel to rise within the tank to second sensor 411. Together, first sensor 410 and second sensor 411 can complement each other to mitigate false alerts while also providing timely alerts of contaminated fuel.

In some embodiments, first sensor 410 and second sensor 411 can both be disposed in fuel inlet 416 to similarly improve accuracy and mitigate false alerts. Alerting system 240 can be configured to deliver an alert if a contamination level associated with a first sensor is outside a predetermined range and a contamination level associated with a second sensor is outside a predetermined range. Likewise, in some embodiments, first sensor 410 and second sensor 411 can both be disposed in aircraft fuel tank 404.

Figure 6:
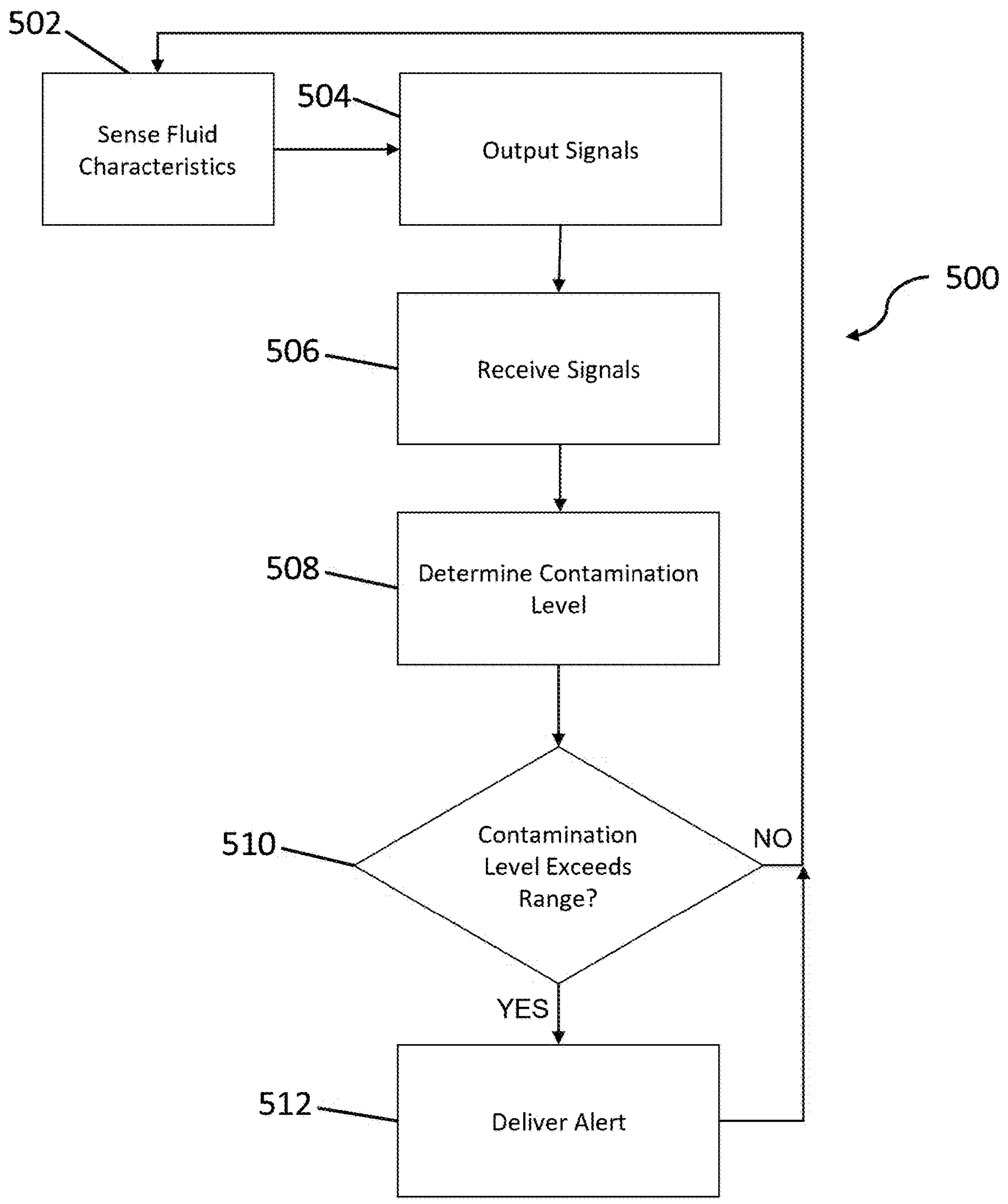
FIG. 6 is a flowchart of a fuel quality monitoring and alerting method according to an embodiment.

In some embodiments, the fuel quality monitoring and alerting system disclosed herein can execute an alerting method 500 resulting in alerting system 240 delivering 512 an alert. As shown in FIG. 6, for example, alerting method 500 can include sensing 502 fluid characteristics. Sensing 502 fluid characteristics can involve measuring the resistance of the fluid, for example, as it passes through fuel inlet 116. In some embodiments, sensing 502 fluid characteristics involves measuring light transmitted through the fluid at a predetermined angle, measuring the pressure of a volume of the fluid, or measuring any other characteristic of a fluid that can indicate the purity, or conversely, the contamination, of that fluid.

For example, measuring the amount of light reflecting through a fluid at a predetermined angle can indicate solid contaminants in the fluid. Further, measuring the amount of light refracting through a fluid can indicate the presence of liquid contaminants. Light can refract through pure fuel at a first angle, but if the fuel tank contains water mixed with the fuel, the light can refract at a second angle different from the first angle, indicating the presence of a liquid contaminants.

After sensing 502 fluid characteristics, alerting method 500 can include outputting 504 signals associated with the fuel characteristics. For example, sensor 110 can output 504 a voltage signal that can be correlated with a resistance of the fluid, the pressure of a volume of the fluid, or the amount of light received by part of sensor 110. Outputting 504 signals can involve outputting one or more signals associated with one or more fluid characteristics that together can be associated with a contamination of the fuel. For example, sensor 110 can output 504 a first signal associated with the amount of light reflected through the fuel at a first angle, and a second signal associated with the amount of light refracted through the fuel at a second angle.

Alerting method 500 can include receiving 506 signals, which can be associated with the contamination of the fuel in aircraft fuel tank 104. In some embodiments, the signals can come from a single sensor. In some embodiments, the signals can come from a first sensor and a second sensor. In some embodiments, processor 112 receives 506 signals and determines 508 a contamination level based on the received signals. Processor 112 can receive 506 multiple output signals 111 per epoch, and can determine 508 multiple contamination levels based on output signals 111, or can determine 508 a single contamination level based on multiple output signals 111. In some embodiments, aircraft 102 includes a first processor configured to receive 506 signals from sensor 110, and a second processor to determine 508 a contamination level based on the received signals. In some embodiments, aircraft 102 includes a first processor configured to receive 506 signals from sensor 110, and a ground control station includes a second processor configured to determine 508 contamination levels based on the received signals. In some embodiments, processor 112 can be integrated on a ground control station, and configured to receive 506 signals from sensor 110, and determine 508 a contamination level of the fuel. As discussed throughout this disclosure, sensor 110 can include one or more sensors of the same or different types.

Alerting method 500 can include evaluating 510 whether the contamination level exceeds a predetermined range. In some embodiments, processor 112 evaluates 510 whether the contamination level exceeds a predetermined range. The predetermined range can be a range of electrical resistance values, a range of pressure values, a range of lumens, and/or a range of values associated with a characteristic of a fluid that can be correlated with the contamination of the fluid. If the contamination level is within the predetermined range, alerting method 500 can restart with sensing 502 fluid characteristics.

If the contamination levels are outside a predetermined range, alerting method 500 can include delivering 512 an alert. In some embodiments, alerting method 500 can include delivering 512 an alert if the contamination levels associated with a first sensor are outside a predetermined range and the contamination levels associated with a second sensor are outside a predetermined range. In some embodiments, alerting system 240 delivers 512 an alert. Alerting system 240 can be executed on processor 112 configured to receive 506 output signals 111, or can be executed on a separate processor. In some embodiments, aircraft 102 can include processor 112, and a ground control station can include alerting system 240. Delivering 512 an alert can involve displaying a text message on display system 244, issuing an aural alert through audio system 246, illuminating a light in pilot interface 114, or any combination therein.

In some embodiments, sensor 110, processor 112, and alerting system 240 can operate at different frequencies. For example, sensor 110 can output 504 signals at 100 Hz, and processor 112 can determine 508 contamination levels and evaluate 510 whether the contamination levels are outside a predetermined range at 1 Hz. By outputting 504 signals at a high rate, sensor 110 can accurately capture the characteristics of the potentially contaminated fuel as it flows into aircraft fuel tank 104. If the rate were too low, sensor 110 might not capture variability in the fuel introduced by water or particulates. Signals output 504 by sensor 110, however, can include noise introduced by, for example, the non-uniform flow of fuel through fuel inlet 116. Processor 112 can determine 508 a contamination level of the fuel by filtering signals it receives 506 from sensor 110, to reduce noise and variability not attributed to contamination. As a result, processor 112 can accurately determine 508 a contamination level and evaluate 510 whether the contamination level is outside a predetermined range. Balancing the rates of sensor 110 and processor 112, or other processors discussed herein, can mitigate potential false alerts that could unnecessarily delay fueling and add time and costs to operating aircraft 102. Although alerting method 500 is described with respect to aircraft 102, alerting method 500 can apply to aircraft 302, and/or any aircraft configured to receive fuel.

Figure 7:
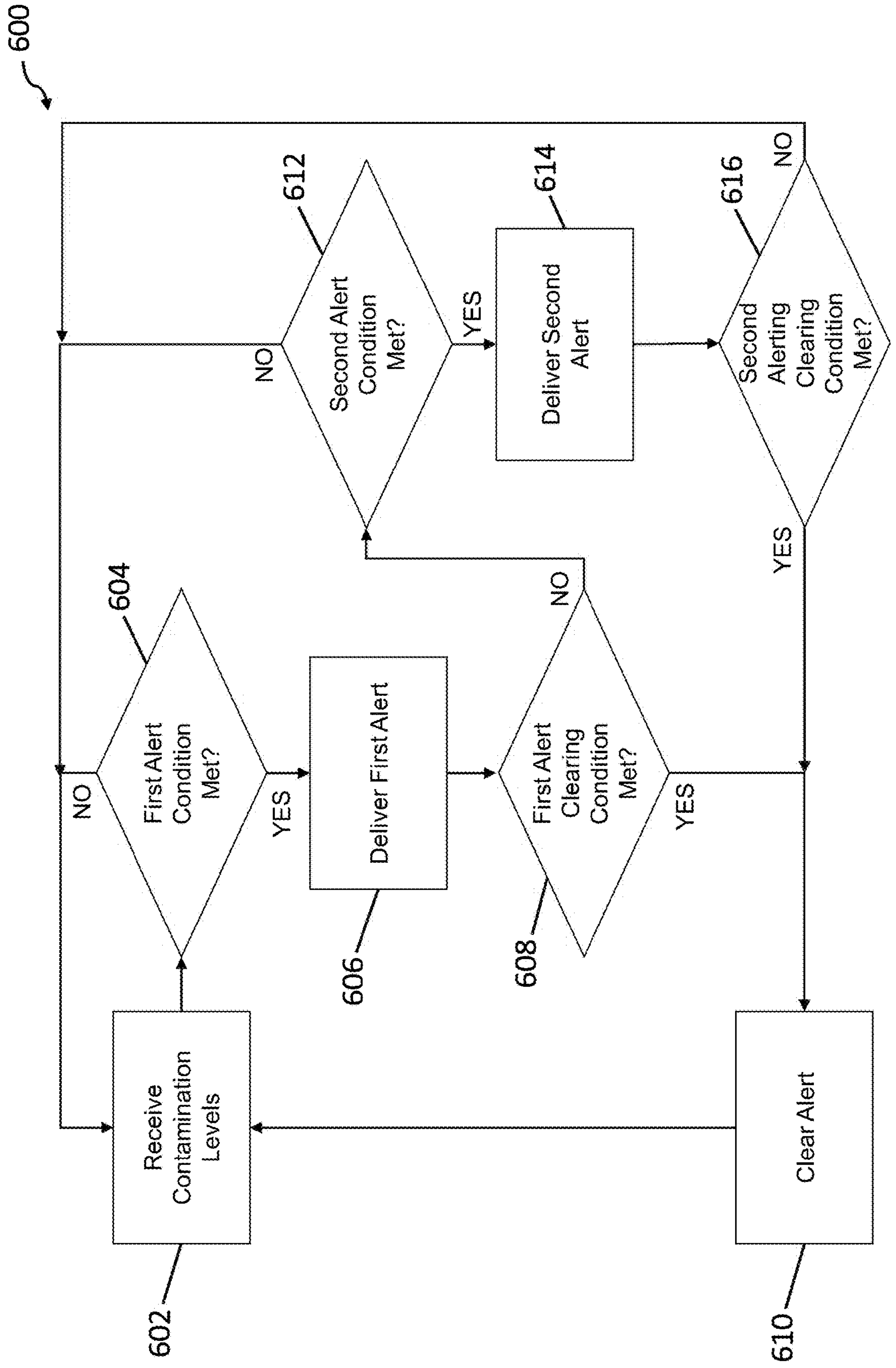
FIG. 7 is a flowchart of an alert sequencing and clearing method for a fuel quality monitoring and alerting system according to an embodiment.

To further provide accurate alerts of contaminated fuel and quickly bring the alert to the attention of the flight crew, the embodiments disclosed herein can include an alert sequencing and clearing method 600. Referring to FIG. 7, alert sequencing and clearing method 600 can include receiving 602 one or more contamination levels. As discussed, processor 112 can receive output signals from sensor 110 and can determine the contamination level based on those signals. In some embodiments, a separate processor can receive 602 contamination levels from processor 112, or a portion of alerting system 240 can be stored in processor 112, and alerting system 240 can receive 602 the contamination level. Processor 112 can execute the remaining steps in alert sequencing and clearing method 600, or a separate processor can execute the remaining steps.

After receiving 602 the contamination level, alert sequencing and clearing method 600 can include evaluating 604 whether a first alert condition is met. In some embodiments, the first alert condition can be met when the contamination level is outside a predetermined range of contamination levels. In some embodiments, the predetermined range can be between 0 PPM of water and 15 PPM of water. In some embodiments, the predetermined range can be between 0 PPM of water and 5 PPM of water, or 0 PPM of water and 10 PPM of water, or 0 PPM of water and 20 PPM of water, or 0 PPM of water and 50 PPM of water. In some embodiments, the first alert condition can be met when the contamination level is outside a predetermined range of contamination levels for a predetermined time period, for example, more than 5 seconds or more than 10 seconds. In some embodiments, the predetermined time period can be between 1 and 20 seconds. For example, alert sequencing and clearing method 600 can evaluate 604 that the first alert condition is met when processor 112 receives 602 a contamination level outside a range between 0 PPM of water and 10 PPM of water for five consecutive seconds. In some embodiments, the first alerting condition can be met when alerting system 240 receives 602 a predetermined number of contamination levels outside a predetermined range. In some embodiments, the predetermined number of contamination levels can be between 1 and 10 contamination levels per epoch. For example, processor 112 can receive 602 five output signals from sensor 110 per second, and can determine five contamination levels. Alert determination system 242 can evaluate 604 that the first alerting condition is met because alerting system 240 received 602 five contamination levels outside a predetermined range of contamination levels. Other time periods, contamination ranges, and/or number of contamination levels can be used. The alert conditions discussed herein can mitigate potential false alerts while timely alerting a flight or ground crew of contaminated fuel.

If alert sequencing and clearing method 600 evaluates 604 that the first alert condition is not met, alert sequencing and clearing method 600 can restart and continue to receive 602 contamination levels. If alert sequencing and clearing method 600 evaluates 604 that the first alert condition is met, alert sequencing and clearing method 600 can include delivering 606 a first alert. As discussed, alerting system 240 can deliver a visual and/or aural alert to a flight or ground crew.

Alert sequencing and clearing method 600 can include evaluating 608 whether a first alert clearing condition is met. In some embodiments, the first alert clearing condition is met when a flight crew commands alerting system 240 to clear the alert by, for example, pressing a button that is part of pilot input system 248 (e.g., push-button or touch screen). In some embodiments, at least a part of pilot input system 248 can be integrated with display system 244. For example, pilot input system 248 can include a pop-up notification on display system 244 that the flight crew can select to clear an alert. In some embodiments, the first alert clearing condition is met when alerting system 240 receives a predetermined number of contamination levels within a predetermined range of contaminations levels, indicating that aircraft 102 is not currently receiving contaminated fuel.

The alert clearing condition can depend on changes in fuel contamination levels. For example, if alerting determination system 242 evaluated 604 that the first alert condition was met based on a single contamination level in the first second of fueling, and then evaluates 604 that the first alert condition is not met for the next ten seconds, alerting system 240 can evaluate 608 that the first alert clearing condition is met. The initial alert may have been a false alert, or may have been associated with a negligible amount of contamination that would not impact engine performance. As another example, if alert determination system 242 evaluates 604 that the first alert condition is met for the first fifteen seconds of fueling, alerting system 240 can evaluate 608 that the alert clearing condition is met only if the flight crew clears the alert. For example, if fuel line 118 connects to a lower portion of fuel source 106, and fuel source 106 contains water and jet fuel, the water may enter aircraft fuel tank 104 before the jet fuel because water is denser than jet fuel. If alerting system 240 automatically clears the alert after receiving uncontaminated fuel for a predetermined period, the flight crew may not be aware that contaminated fuel entered aircraft fuel tank 104 first. Maintaining the alert until the flight crew clears it can ensure the flight crew sees the alert.

In some embodiments, if alerting system 240 evaluates 608 first alerting clearing condition is met, alerting system 240 can clear 610 the alert. For example, alerting system 240 can update display system 244 to no longer display a text alert, or can stop commanding audio system 246 to deliver aural alerts. After clearing 610 the alert, alert sequencing and clearing method 600 can restart by continuing to receive 602 contamination levels.

If alerting system 240 evaluates 608 that the first alert clearing condition is not met, alert sequencing and clearing method 600 can include evaluating 612 if a second alert condition is met. If alerting system 240 evaluates 612 that the second alert condition is not met, alert sequencing and clearing method 600 can restart to continue receiving 602 contamination levels. If alerting system 240 evaluates 612 that the second alert condition is met, alerting system 240 can deliver 614 a second alert. In some embodiments, the second alert condition can be the same as the first alert condition. In some embodiments, the second alert condition is different from the first alert condition. For example, alerting system 240 can deliver 606 a first alert if the contamination level is outside a predetermined range for a first predetermined time period, and alerting system 240 can deliver 614 a second alert if the contamination level is outside the predetermined range for a second predetermined time period. As another example, alerting system 240 can deliver 606 a first alert if the contamination level is outside a first predetermined range, and alerting system 240 can deliver 614 a second alert if the contamination level is outside a second predetermined range that is different from the first predetermined ranged. In some embodiments, the first alert is a different type of alert than the second alert. For example, the first alert can be a visual alert on display system 244 and the second alert can be an aural alert issued through audio system 246. Sequencing a first alert and a second alert based on different time periods or predetermined ranges of contamination levels can alert the flight crew of varying severity of contaminated fuel, and can alert the flight crew without unnecessarily interfering with other pre-flight operations, or causing panic.

In some embodiments, alert sequencing and clearing method 600 can include evaluating 616 if the second alert clearing condition is met, and clearing 610 the second alert if the second alert clearing condition is met. In some embodiments, the second alert clearing condition can be satisfied in the same manner as the first alert clearing condition. For example, the first and second alert clearing condition can be met when the flight crew presses a button that is part of pilot input system 248. In other embodiments, the second alerting clearing condition can be met in a different manner than the first alert clearing condition. For example, if the first alert is associated with a lower contamination level than the second alert, alerting system 240 can evaluate 608 that the first alert clearing condition is met when contamination levels are within a predetermined range for a predetermined period. By contrast, alerting system 240 can evaluate 616 that the second alert clearing condition is met when the flight crew presses a button that is part of the pilot input system 248. Distinct alert clearing conditions can help ensure the flight crew responds to the alerts of contaminated fuel, without unnecessarily interfering with pre-flight operations if the contamination is insignificant.

The embodiments disclosed herein can further comprise memory configured to store information associated with an alert. The information associated with an alert can include the time of the alert, an identifier indicating the type of alert (e.g., advisory or warning, and first or second alert), an identifier indicating the first alert condition, an identifier indicating the second alert condition, output signals 111, contamination level(s), aircraft type, or any other parameter relevant to the alert. Storing the alert and information associated with the alert can help improve the system, provide training to flight crews, and to share data with fuel providers.

Although the embodiments disclosed herein are described in the context of alerting a flight crew of contaminated fuel as fuel enters aircraft fuel tank 104, the systems and methods can be applied during taxi and flight to similarly alert the flight crew. In response to an alert issued during taxi or flight, a flight crew can abort takeoff or land as soon as is safely possible. Further, although the embodiments disclosed herein reference alerting a flight crew, the embodiments can also include alerting a fueling crew, maintenance crew, or any personnel monitoring aircraft fueling.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. An aircraft-based fuel quality monitoring system, comprising:

- a sensor configured to output a signal associated with contamination of fuel entering an aircraft fuel tank;
- a processor configured to determine whether the fuel entering the aircraft fuel tank is contaminated based on the signal;
- an input system; and
- an alerting system configured to deliver an alert if the fuel entering the aircraft fuel tank is contaminated,
- wherein the alerting system is configured to deliver the alert until the alert is extinguished from a display system or an audio system by an input on the input system.

2. The aircraft-based fuel quality monitoring system of claim 1, wherein the processor is configured to determine that the fuel entering the aircraft fuel tank is contaminated based on a change in a fuel type entering the aircraft fuel tank.

3. The aircraft-based fuel quality monitoring system of claim 1, wherein the processor is configured to determine that the fuel entering the aircraft fuel tank is contaminated if the fuel entering the aircraft fuel tank is an improper fuel type.

4. The aircraft-based fuel quality monitoring system of claim 3, wherein the aircraft comprises a jet-engine, and wherein the improper fuel type is Avgas.

5. The aircraft-based fuel quality monitoring system of claim 3, wherein the aircraft comprises a piston engine, and wherein the improper fuel type is turbine fuel.

6. The aircraft-based fuel quality monitoring system of claim 1, wherein the processor is configured to determine a contamination level of the fuel entering the aircraft fuel tank, and wherein the processor is configured to determine that the fuel entering the aircraft fuel tank is contaminated if the contamination level is outside a predetermined range.

7. The aircraft-based fuel quality monitoring system of claim 6, wherein the predetermined range comprises an amount of a contaminant.

8. The aircraft-based fuel quality monitoring system of claim 7, wherein the contaminant is water, and wherein the predetermined range is between 0 PPM of water and 20 PPM of water.

9. The aircraft-based fuel quality monitoring system of claim 6, wherein the predetermined range is at least one of a range of electrical resistance values, a range of pressure values, or a range of lumens.

10. The aircraft-based fuel quality monitoring system of claim 9, wherein the processor is configured to determine whether the fuel entering the aircraft fuel tank is contaminated based on at least two of the electrical resistance of the fuel entering the aircraft fuel tank, the pressure of the fuel entering the aircraft fuel tank, or the amount of light received by the sensor.

11. The aircraft-based fuel quality monitoring system of claim 1, wherein the signal corresponds to at least one of an electrical resistance of the fuel entering the aircraft fuel tank, a pressure of the fuel entering the aircraft fuel tank, or an amount of light received by the sensor.

12. The aircraft-based fuel quality monitoring system of claim 1, wherein the alerting system is configured to deliver the alert as fuel continues entering the aircraft fuel tank.

13. An aircraft comprising:

a sensor configured to output a signal associated with contamination of fuel entering the aircraft through a fuel inlet;

a processor configured to determine a contamination level of the fuel based on the signal from the sensor; and an alerting system configured to deliver an alert to a pilot interface if the contamination level is outside a predetermined range of contamination levels, wherein the predetermined range of contamination levels is based on a first fuel type, and wherein the alerting system is configured to deliver the alert until an alert clearing condition is satisfied.

14. The aircraft of claim 13, wherein the alert clearing condition is satisfied based on a change in the contamination level of the fuel entering the aircraft.

15. The aircraft of claim 13, wherein the alert clearing condition is satisfied when the contamination level is outside the predetermined range for a first time period and the contamination level is inside the predetermined range for a second time period, and wherein the second time period is greater than the first time period.

16. The aircraft of claim 13, wherein the alert clearing condition is satisfied by an input on a pilot input system.

17. The aircraft of claim 16, wherein the pilot input system comprises a touch screen or a push button disposed inside the aircraft.

18. The aircraft of claim 13, wherein the pilot interface is inside the aircraft.

19. The aircraft of claim 18, wherein the pilot interface comprises at least one of a primary flight display, a secondary flight display, a multi-function display, an ADS-B display, a multi-function control and display unit, or a heads-up display.

20. The aircraft of claim 13, wherein the pilot interface comprises an electronic flight bag.

21. The aircraft of claim 13, wherein the aircraft is a remotely piloted aircraft, and wherein the pilot interface is located at a ground control station.

22. The aircraft of claim 13, wherein the predetermined range of contamination levels is between 0 PPM of water and 15 PPM of water.

23. An aircraft-based fuel quality monitoring system, comprising:

a sensor configured to output a signal associated with contamination of fuel entering the aircraft through a fuel inlet;

a processor configured to determine a contamination level of the fuel based on the signal from the sensor; and an alerting system configured to deliver an alert to a pilot interface if the contamination level is outside a predetermined range, wherein the alerting system is configured to deliver the alert until an alert clearing condition is satisfied, and wherein the alert clearing condition is satisfied based on a change in the contamination level of the fuel entering the aircraft.

24. The aircraft-based fuel quality monitoring system of claim 23, wherein the alert clearing condition is satisfied when the contamination level is outside the predetermined range for a first time period and the contamination level is inside the predetermined range for a second time period, and wherein the second time period is greater than the first time period.

25. The aircraft-based fuel quality monitoring system of claim 24, wherein the alert clearing condition is satisfied when the contamination level is outside the predetermined range for a first group of contamination levels and the contamination level is inside the predetermined range for a second group of contamination levels, and wherein the second group comprises more contamination levels than the first group.

* * * * *